United States Patent
Amoros et al.

(10) Patent No.: US 10,421,247 B2
(45) Date of Patent: Sep. 24, 2019

(54) CHECKING DEVICE AND METHOD FOR CHECKING THE QUALITY OF FOLDABLE BOXES, AND MANUFACTURING INSTALLATION COMPRISING THIS CHECKING DEVICE

(71) Applicant: BOBST LYON, Villeurbanne (FR)

(72) Inventors: Robert Amoros, Villette d'Anthon (FR); Benoît Rosset, Thoiry (FR)

(73) Assignee: BOBST LYON (FR)

( * ) Notice: Subject to any disclaimer, the term of this patent is extended or adjusted under 35 U.S.C. 154(b) by 138 days.

(21) Appl. No.: 15/536,374

(22) PCT Filed: Dec. 17, 2015

(86) PCT No.: PCT/EP2015/025107
§ 371 (c)(1),
(2) Date: Jun. 15, 2017

(87) PCT Pub. No.: WO2016/096157
PCT Pub. Date: Jun. 23, 2016

(65) Prior Publication Data
US 2017/0348940 A1    Dec. 7, 2017

(30) Foreign Application Priority Data

Dec. 19, 2014    (FR) ..................................... 14 62881

(51) Int. Cl.
*B07C 5/342* (2006.01)
*B31B 50/00* (2017.01)
(Continued)

(52) U.S. Cl.
CPC .............. *B31B 50/81* (2017.08); *B07C 5/342* (2013.01); *B31B 50/003* (2017.08);
(Continued)

(58) Field of Classification Search
None
See application file for complete search history.

(56) References Cited

U.S. PATENT DOCUMENTS 5,212,656 A * 5/1993 Clary ..................... G01B 11/04
702/84
6,484,066 B1 * 11/2002 Riess ..................... G01B 11/00
198/502.2
(Continued)

FOREIGN PATENT DOCUMENTS

DE    10 2009 053 561 A1    6/2010
DE    10 2011 101 252 A1    11/2012
(Continued)

OTHER PUBLICATIONS

International Search Report dated Mar. 14, 2016 in corresponding PCT International Application No. PCT/EP2015/025107.
(Continued)

*Primary Examiner* — Soo Shin
(74) *Attorney, Agent, or Firm* — Ostrolenk Faber LLP (57) ABSTRACT

A quality-control device (200) includes: an illumination system (202) for illuminating one peripheral face of each folding box, an image capture device (204) for forming a multiple image of the respective peripheral faces of a bundle of folding boxes, an image processing system (206) for: i) detecting within the multiple image each peripheral end of the slots of each box that separate its adjacent flaps, ii) generating a data set indicative of the geometry of each peripheral end, and iii) analyzing the data set to determine the width of each peripheral end.

12 Claims, 5 Drawing Sheets

(51) Int. Cl.
*B31B 50/98* (2017.01)
*G01B 11/02* (2006.01)
*G01N 21/86* (2006.01)
*G01N 21/88* (2006.01)
*B31B 50/81* (2017.01)
*B31B 100/00* (2017.01)
*B31B 120/30* (2017.01)
*B31B 110/35* (2017.01)

(52) U.S. Cl.
CPC ............ *B31B 50/006* (2017.08); *B31B 50/98* (2017.08); *G01B 11/02* (2013.01); *G01N 21/86* (2013.01); *G01N 21/8851* (2013.01); *B31B 2100/00* (2017.08); *B31B 2100/0022* (2017.08); *B31B 2110/35* (2017.08); *B31B 2120/30* (2017.08)

(56) References Cited

U.S. PATENT DOCUMENTS 8,073,239 B1 * 12/2011 Bahrami ................ G06T 7/001
                                                                    382/141
2001/0016059 A1 * 8/2001 Krahn ................ G01N 21/9508
                                                                    382/141
2015/0070487 A1 * 3/2015 Agbuga ............. G01N 21/6489
                                                                    348/126

FOREIGN PATENT DOCUMENTS

| EP | 0 892 264 A2 | 1/1999 | |
|---|---|---|---|
| EP | 0 937 573 A1 | 8/1999 | |
| JP | H09-22464 A | 1/1997 | |
| WO | WO 2013/118080 A1 | 8/2013 | |
| WO | WO-2013118080 A1 * | 8/2013 | ............. B31B 50/00 |

OTHER PUBLICATIONS

Written Opinion dated Mar. 14, 2016 in corresponding PCT International Application No. PCT/EP2015/025107.

* cited by examiner

CHECKING DEVICE AND METHOD FOR CHECKING THE QUALITY OF FOLDABLE BOXES, AND MANUFACTURING INSTALLATION COMPRISING THIS CHECKING DEVICE

CROSS-REFERENCE TO RELATED APPLICATIONS

The present application is a 35 U.S.C. §§ 371 national phase conversion of PCT/EP2015/025107, filed Dec. 17, 2015, which claims priority of French Patent Application No. 1462881, filed Dec. 19, 2014, the contents of which are incorporated by reference herein. The PCT International Application was published in the French language.

TECHNICAL FIELD

The present invention relates to a checking device and method for checking the quality of foldable boxes. The present invention also relates to a manufacturing installation comprising a checking device of this kind.

TECHNICAL BACKGROUND

The present invention is applicable to the fields of manufacturing and checking foldable boxes. A foldable box may, for example, be a cardboard packaging box. As a general rule, a foldable box in the folded state comprises a plurality of panels joined together by folds, and a plurality of flaps joined to the panels. Two neighboring flaps are separated by a slot extending between a central region and a peripheral face of the foldable box. The slot has a peripheral end opening on the peripheral face and delimiting a lateral interval between the two neighboring flaps.

In the prior art, an installation for manufacturing foldable boxes comprises a gluing device, a device for folding the panels of each foldable box, a stacking device for stacking the foldable boxes, and a conveying device for moving each foldable box between the gluing, folding and stacking devices.

EP0937573A1 discloses a checking device comprising an illumination system for illuminating each foldable box and a camera for forming images of each foldable box, one by one, in the course of movement by a roller conveyor means. The function of a checking device of this kind is, notably, to determine whether each foldable box does or does not conform to the established specifications.

However, the checking device of EP0937573A1 is placed at a location where the foldable box has not yet undergone all the specified processes. Thus, after the camera has formed an image of the slots separating the flaps, each foldable box undergoes other processes which may modify the state of the foldable box. It may happen, therefore, that the checking device of EP0937573A1 assesses a foldable box as non-conforming even though this foldable box could have become conforming after squaring. Therefore, using the checking device of EP0937573A1 results in a relatively large number of rejected foldable boxes.

SUMMARY OF THE INVENTION

The object of the present invention is, notably, to overcome some or all of the aforementioned problems, by providing a checking device that can reduce the risks of error by the checking device, and therefore the number of foldable boxes rejected.

To this end, the invention proposes a checking device for checking the quality of foldable boxes, each foldable box comprising, when the foldable box is in the folded state, at least two flaps separated by a slot. The slot has a peripheral end opening on a peripheral face of the foldable box and delimits a lateral interval between the two flaps, the checking device comprising:

an illumination system for illuminating the foldable boxes in the folded state, and at least one imaging device for forming images of the foldable boxes in the folded state, the checking device being characterized in that:

the illumination system is configured to illuminate a pack formed of superimposed or juxtaposed foldable boxes, the pack having at least one peripheral pack face defined by respective peripheral faces of all the foldable boxes composing the pack, the at least one imaging device is configured to form at least one plural image representing at least a part of the peripheral pack face when the illumination system illuminates the peripheral pack face, and at least one image processing system configured for:
i) detecting each peripheral end in the plural image,
ii) generating a set of data representing the geometry of each peripheral end, and
iii) analyzing the set of data so as to determine the width of each lateral interval.

This checking device therefore checks a plurality of foldable boxes simultaneously after they have been arranged in packs and squared, enabling the risks of error to be reduced. This is because this checking in packs can decrease the number of foldable boxes rejected, since the squaring of a pack sometimes rectifies some of the foldable boxes which would have been considered defective if they had been checked individually. A checking device of this kind can be placed on one side of a foldable box conveyor device belonging to the foldable box manufacturing installation, thereby reducing the overall dimensions of the manufacturing installation.

In the present application, the term "plural image" denotes an image representing the peripheral faces of a plurality of foldable boxes, for example those of a plurality of foldable boxes which have been combined, that is to say superimposed or juxtaposed.

In the present application, the term "pack" denotes a group formed by a plurality of foldable boxes combined with one another. A pack may be, for example, a stack of foldable boxes in the folded state which have been superimposed, or a group of foldable boxes in the folded state which have been juxtaposed. In the case of a stack, the foldable boxes forming the pack are not necessarily tied together. In the case of a stack, the foldable boxes are substantially horizontal. In the case of a group, the foldable boxes are stacked beforehand by the stacking device, then tied together by a tying device, after which the pack is pivoted, through a quarter turn for example. In the case of a group, the foldable boxes may be substantially vertical.

In the present application, the term "lateral" denotes a side of a foldable box or of a pack of foldable boxes. Typically, the edge of a foldable box forms a lateral face of this foldable box.

According to one embodiment of the invention, the image processing system is also configured for:
iv) extracting dark objects from each plural image,
v) comparing the height of each dark object with the nominal thickness of a foldable box in the folded state, the height being measured perpendicularly to the largest dimension of the foldable box in the folded state, and vi) selecting each dark object having a height equivalent to the nominal thickness of a foldable box in the folded state subject to a predetermined tolerance, each selected dark object corresponding to a lateral interval.

This image processing system therefore automatically finds the locations of the peripheral ends of the slots. On each selected dark object, the image processing system can determine the width of the lateral interval formed at the peripheral end of each slot.

According to a variant of the invention, the image processing system is also configured for:

a) detecting the boundaries of the peripheral face perpendicularly to the largest dimension of the foldable box in the folded state, b) measuring a reference level of brightness between one of said boundaries and an edge of the image of the peripheral face, and c) generating a binary image by using this reference brightness level to perform a thresholding operation on the image of the peripheral face.

According to a variant of the invention, the image processing system comprises a memory configured to record geometrical parameters of the foldable boxes, in particular the nominal thickness of the foldable boxes.

A dark object is an object which does not reflect, or reflects only a small part of, the illumination emitted by the illumination system. A dark object may thus appear substantially black on the image of the peripheral face. In other words, the pixels forming a dark object have a brightness level, for example a gray level, which is low or zero. Thus a dark object corresponds to an empty or low-density region of the foldable box, for example the peripheral end of a slot, or a corrugation if the foldable box comprises a corrugated sheet.

According to a variant of the invention, the predetermined tolerance is selected from between 3% and 50% of the nominal thickness of a foldable box in the folded state.

According to one embodiment of the invention, the image processing system is also configured for:

vii) detecting, in each plural image, the boundaries of the foldable boxes forming the ends of the pack perpendicularly to the largest dimension of a foldable box in the folded state, and viii) discriminating each foldable box in the pack.

This image processing system can therefore be used to determine, in a single image processing stage, the lateral intervals of the slots of all the foldable boxes appearing in a plural image.

According to a variant of the invention, the image processing system carries out the discrimination of each foldable box by processing the binary image generated as specified above. The image processing system can then compare the height of each dark object with the nominal thickness of a foldable box in the folded state, and can then select each dark object having a height equivalent to the nominal thickness of a foldable box in the folded state, subject to a predetermined tolerance. The image processing system then generates the set of data representing the geometry of the peripheral ends, so as to determine the width of each lateral interval, for all the foldable boxes appearing in the plural image.

According to one embodiment of the invention, the image processing system is also configured for:

ix) comparing the width of each lateral interval with a predetermined lower limit and a predetermined upper limit, and x) generating an anomaly signal if a width of a lateral interval is either below the predetermined lower limit or above the predetermined upper limit.

This image processing system can therefore be used to signal any defective foldable box, that is to say a box having a lateral interval which is too large or too small as a result of defective cutting, folding and/or gluing.

According to a variant of the invention, the anomaly signal is associated with a data element identifying the defective foldable box. Thus an operator can rapidly pick out and reject the defective foldable box.

According to one embodiment of the invention, the at least one imaging device is a matrix camera. According to a variant of the invention, the matrix camera is polychromatic. According to a variant of the invention, the matrix camera is monochromatic.

The camera, or each camera, can be arranged movably so as to descend toward the conveying device, such as a conveyor, which moves the packs, so that the camera, or each camera, checks each pack. The camera, or each camera, then rises again between two packs, so as to free the path for the next packs.

According to one embodiment of the invention, said at least one imaging device is a line scan camera configured to form an image of a respective peripheral face of each foldable box while a conveying device moves each foldable box relative to the line scan camera.

This line scan camera can therefore be used to form images of peripheral faces while the conveying device is moving the foldable boxes. Since the movement of the foldable boxes is not interrupted, the rate of production of the foldable boxes can be high. The line scan camera is advantageously synchronized with the speed of the movement of the foldable boxes by a conveying device of the manufacturing installation.

According to one embodiment of the invention, the checking device comprises at least two imaging devices placed at two different heights, so as to form plural images of a lower part and an upper part, respectively, of the peripheral pack face.

The zero height can be considered to be near the imaging devices and on a surface of the conveying device intended to receive a foldable box.

Thus the two imaging devices can be used to form high-resolution plural images, even if the packs contain large numbers of foldable boxes.

According to a variant of the invention, the two imaging devices are configured for producing an overlap area between a plural image of the lower part of the pack and a plural image of the upper part of the pack. This overlap area therefore ensures that no foldable box in the pack can be missed by the checking device or be counted twice.

As an alternative to a camera, the imaging device may be a photographic camera. This photographic camera can therefore form photographic images when a device for conveying packs of foldable boxes stops or slows down. To use this alternative, the conveying device must be controlled so that stops can be distinguished regularly, for example on each passage of a pack of foldable boxes.

According to one embodiment of the invention, the illumination system comprises at least one illumination source selected from the group consisting of fluorescent tubes, discharge lamps and light-emitting diodes, for example a column of light-emitting diodes.

This illumination source can therefore be used to illuminate the foldable boxes effectively so as to form high-contrast images of peripheral faces. Since this illumination source may emit a large amount of light, the plural images are high-contrast, so that the peripheral ends of said foldable boxes can be precisely detected.

According to one embodiment of the invention, the illumination system is configured to illuminate in a pulsed manner a peripheral face of each foldable box in the folded state.

This pulsed illumination system can therefore be used to illuminate the foldable boxes with a large amount of light, so as to form high-contrast images of peripheral faces. Since this illumination source may emit a large amount of light, the plural images are high-contrast, so that the peripheral ends of said foldable boxes can be precisely detected.

According to a variant of the invention, the duration of an illumination pulse is in the range from 0.01 ms to 100 ms, for example 1 ms.

According to one embodiment of the invention, the illumination system comprises two illumination sources arranged on either side of said at least one imaging device, the illumination sources being configured for the successive illumination of the same peripheral face of each foldable box in the folded state, so that the at least one imaging device successively forms two different images of the same peripheral face of each foldable box in the folded state.

In other words, the illumination system provides alternating illumination on the left and right of the imaging device, which forms two images having different contrast levels depending on the location in the image. These two images can therefore be used for the precise identification of the edges of V-shaped slots. This is because the first image (seen from the left) has high contrast for the left boundaries of the peripheral end of the slot, whereas the second image (seen from the right) has high contrast for the right boundaries of the peripheral end of the slot.

The present invention also proposes a manufacturing installation for manufacturing foldable boxes, and when the foldable box is in the folded state, each foldable box comprises panels linked by folds and at least two flaps separated by a slot, the manufacturing installation comprising at least:

a gluing device configured to apply glue to a gluing area of each foldable box, a folding device configured to fold panels so as to glue an area to be glued onto the gluing area, a stacking device configured for stacking the foldable boxes in the folded state, a conveying device, configured to place each foldable box at the gluing device, then at the folding device, then at the stacking device, and at least one checking device according to the invention, the at least one checking device being placed downstream of the stacking device.

This manufacturing installation can therefore be used to manufacture foldable boxes at a high production rate, with a very low rejection rate, notably because each imaging device forms high-contrast images, thereby reducing the risk of error by the checking device, and consequently the number of foldable boxes rejected. Each checking device can check all the foldable boxes appearing in a plural image in a single phase.

In other words, the gluing device, the folding device and the stacking device follow one another from the upstream to the downstream end, in the direction of circulation determined by the conveying device. In this embodiment, the checking device checks the foldable boxes in packs.

According to a variant of the invention, the conveying device is a conveyor, for example a belt conveyor. According to a variant of the invention, the conveying device is regulated so that the output rate of the installation is between 1000 and 2500 foldable boxes per hour, for example 1800 foldable boxes per hour.

According to one embodiment of the invention, the manufacturing installation of the previous embodiment comprises two checking devices, the checking devices being arranged so as to form respective images of two peripheral pack faces.

In this arrangement, the two imaging devices are separated by a distance which is predetermined, notably on the basis of the width of the packs. This arrangement of the two checking devices can therefore be used to check the slots located on each peripheral pack face simultaneously.

According to an alternative to the previous embodiment, the manufacturing installation comprises a single checking device and a rotary mechanism configured to make each pack of foldable boxes pivot through a half-turn. Thus the checking device can check the opposite faces of each pack of foldable boxes successively. With a single checking device, the overall dimensions of the manufacturing installation are reduced.

According to a variant of the invention, the checking device can be positioned in line; that is, the checks are made when the conveying device brings the foldable boxes to a position in front of the checking device. Alternatively, the checking device can be positioned off line; that is, the foldable boxes are checked after they have been removed from the conveying device.

According to a variant of the invention, the conveying device is arranged to convey the packs of foldable boxes in a horizontal direction, and the checking device is arranged so that the orientation of the light source of the at least one illumination system forms an angle in the range from 0 degrees to 70 degrees with the horizontal direction.

According to a variant of the invention, the manufacturing installation may comprise an ejection mechanism configured to eject the packs individually, the ejection mechanism being connected to the checking device, and in particular to the image processing system, so that, when the checking device emits a fault signal indicating that a pack contains at least one defective foldable box, the ejection mechanism ejects the pack containing at least one defective foldable box.

Additionally, the present invention proposes a checking method for checking the quality of foldable boxes, and when the foldable box is in the folded state, each foldable box comprises at least two flaps separated by a slot, the slot having a peripheral end opening on a peripheral face of the foldable box and the slot delimiting a lateral interval between the two flaps, the checking method comprising the steps of:

illuminating, by means of an illumination system, the foldable boxes in the folded state, the checking method further comprises the steps of:

illuminating, by means of the illumination system, a pack formed of superimposed or juxtaposed foldable boxes, the pack having at least one peripheral pack face defined by the respective peripheral faces of all the foldable boxes composing the pack, forming, by means of the at least one imaging device, images of the foldable boxes in the folded state, and at least one plural image representing at least a part of the peripheral pack face when the illumination system illuminates the peripheral pack face, actuating at least one image processing system for the purpose of:
i) detecting at least one peripheral end in the plural image,
ii) generating a set of data representing the geometry of each peripheral end, and
iii) analyzing the set of data so as to determine the width of each lateral interval.

The aforementioned embodiments and variants may be considered separately or in any technically feasible combination.

The present invention will be readily understood and its advantages will be apparent in the light of the following description, provided solely by way of non-limiting example, with reference to the attached figures, in which:

DESCRIPTION OF EMBODIMENTS

Figure 1:
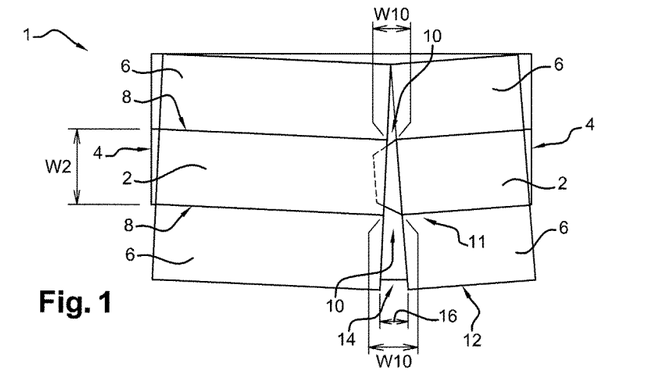
FIG. 1 is a schematic view illustrating a defective foldable box.

FIG. 1 shows a foldable box 1 in the folded state, comprising i) panels 2 which are linked by folds 4, together with ii) flaps 6. Each panel 2 has a width W2, measured perpendicularly to the folds 4, corresponding to the height of the foldable box 1 in the unfolded state. Each flap 6 is linked to a respective panel 2 by a fold 8 formed by a corrugating machine.

Two neighboring flaps 6 are separated by a respective slot 10. Each slot 10 extends between a central region 11 and a peripheral face 12 of the foldable box 1. The slot 10 has a peripheral end 14 opening on the peripheral face 12 and delimiting a lateral interval 16 between the two neighboring flaps 6. The slot 10 has a central end located in the central region 11, and therefore opposite to the peripheral end 14.

As shown in FIG. 1, the foldable box 1 has a fault, because the slots 10 have oblique edges, instead of edges parallel to one another. One of the slots 10 has an excessively wide peripheral end 14, and therefore an excessively large lateral interval 16, while the other slot 10 has an excessively narrow peripheral end 14, and therefore an excessively small lateral interval 16. This fault may be due to incorrect cutting, incorrect gluing and/or incorrect folding. Sometimes, a width W10 of a slot 10 is determined near the folds 8, by measurement in a prior art device, or by extrapolation in the case of the present invention.

Figure 2:
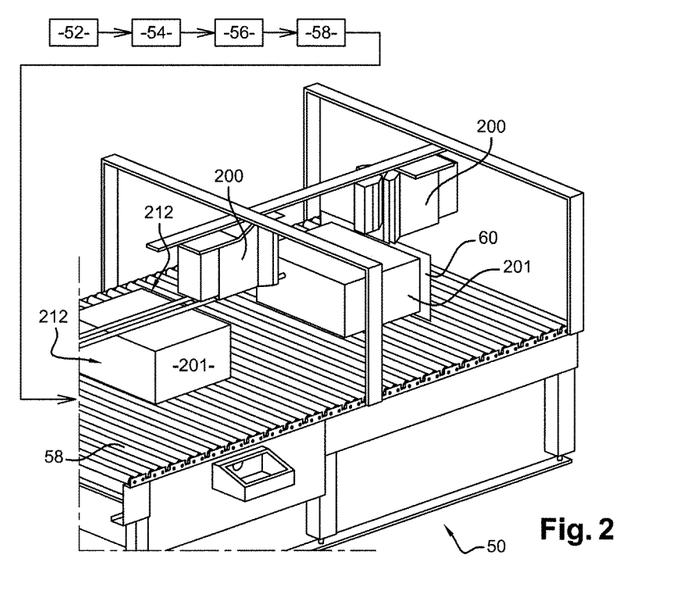
FIG. 2 is a schematic view of a manufacturing installation according to the invention.

FIG. 2 shows a manufacturing installation 50 intended to manufacture foldable boxes 1 and comprising at least:
a gluing device 52 configured to apply glue to a gluing area of each foldable box 1,
a folding device 54 configured to fold panels 4 so as to glue an area to be glued onto the gluing area,
a stacking device 56 configured for stacking the foldable boxes 1 in the folded state,
a squaring device 60 configured for squaring the foldable boxes 1 so as to form packs 201,
a conveying device 58, configured to place the foldable boxes 1 in the gluing device 52, then in the folding device 54, then in the stacking device 56; in this case, the conveying device 58 is a belt conveyor providing an output rate of the installation equal to about 1800 foldable boxes 1 per hour, and
two checking devices 200 according to the invention.

Figure 3:
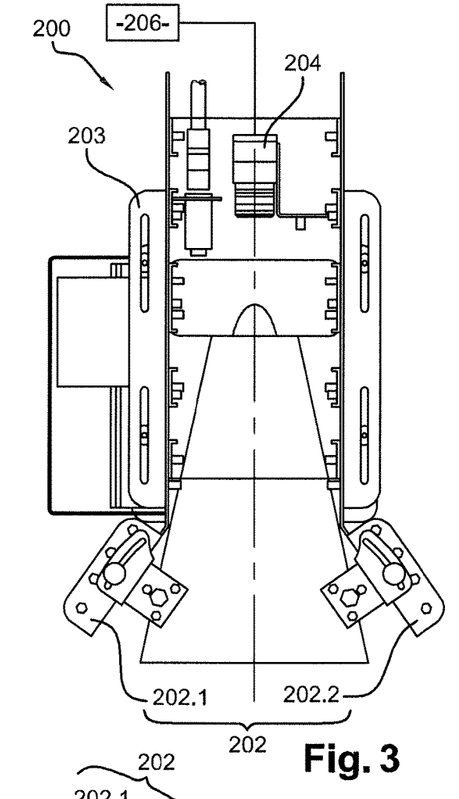
FIG. 3 is a schematic top view of a part of the manufacturing installation of FIG. 2, comprising a checking device according to a first embodiment of the invention.

In the example of FIGS. 2 and 3, the checking devices 200 are placed downstream of the stacking device 56 and of the squaring device 60. The gluing device 52, the folding device 54, the stacking device 56 and the squaring device 60 follow one another from the upstream to the downstream end, in the direction of circulation determined by the conveying device 58. Each checking device 200 therefore checks the foldable boxes 1 in packs 201.

Additionally, the two checking devices 200 are arranged so as to form respective images of two peripheral pack faces 212, particularly the two opposite faces of each pack onto which the respective slots open and where the interval of the flaps at each face are seen and measured. This arrangement can be used to check all the slots of each foldable box 1 contained in a pack 201.

FIGS. 3, 4, 5 and 6 show one of the checking devices 200. The checking device 200 comprises an illumination system 202 with two illumination sources 202.1 and 202.2, two cameras 204 forming an imaging device, and an image processing system 206. The illumination system 202 and the cameras 204 are mounted on a framework 203.

In this case, the checking device 200 is positioned in line; that is to say, the checks are made when the conveying device 58 brings the packs 201 to a position in front of the checking device 200. The conveying device 58 is arranged to convey the packs 201 in a horizontal direction.

The illumination system 202 is configured to illuminate a pack 201 formed from superimposed foldable boxes, wherein the illumination system 202 is configured to illuminate the foldable boxes 1 one by one. The pack 201 has two peripheral pack faces 212 on which the slots 210 open, which are defined by peripheral faces of all the foldable boxes composing the pack 201. The solid angle illuminated by one illumination system 202.1 is therefore larger than the solid angle illuminated by the other illumination system 202.2.

Figure 6:
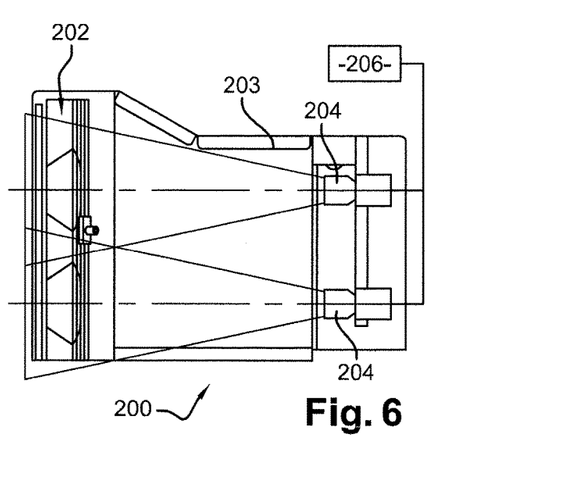
FIG. 6 is a schematic cross section, in a vertical plane when the checking device is in the operating position, of the checking device of FIG. 4.

As shown in FIG. 6, the checking device 200 comprises two cameras 204. The cameras 204 are placed at two different heights, so as to form plural images 205 of a lower part and an upper part, respectively, of the peripheral pack face 212.

Thus the two cameras 204 can be used to form high-resolution plural images 205, even if the packs 201 contain large numbers of foldable boxes 1. In this case, the cameras 204 are configured for producing an overlap area between a plural image of the lower part of the pack 201 and a plural image of the upper part of the pack 201. The checking device 200 is arranged so that the optical axis of each camera 204 forms an angle (not shown) of about 60 degrees to the horizontal direction.

Each camera 204 is a matrix camera, while the camera 204 may be a line scan camera.

Each camera 204 is configured to form at least one plural image 205 (FIGS. 8 and 10) of the peripheral pack face 212 when the illumination system 202 illuminates the peripheral pack face 212. Each plural image 205 represents at least a part of the peripheral pack face 212 when the illumination system 202 illuminates the peripheral pack face 212. FIGS. 8, 10, 13, 14 and 16 show equivalent plural images 205. The field of view of one camera 204 is therefore greater than the field of view of the other camera 204.

Figure 4:
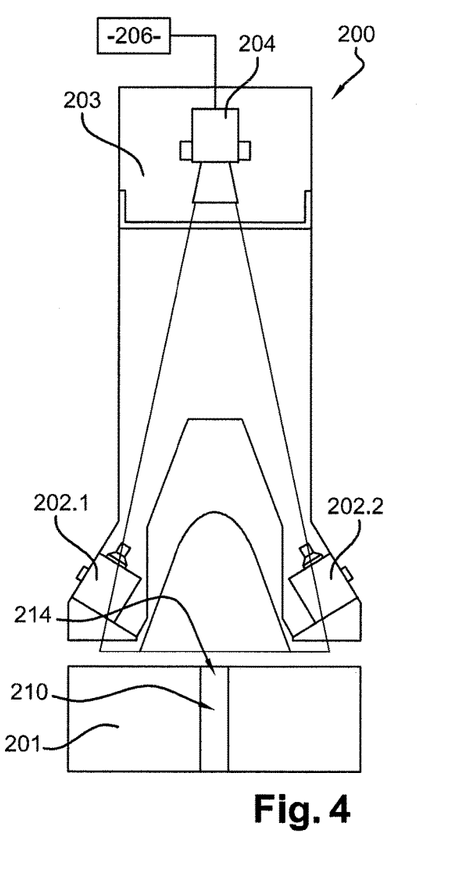
FIG. 4 is a schematic cross section in a horizontal plane when the checking device of FIG. 3 is in the operating position.
Figure 5:
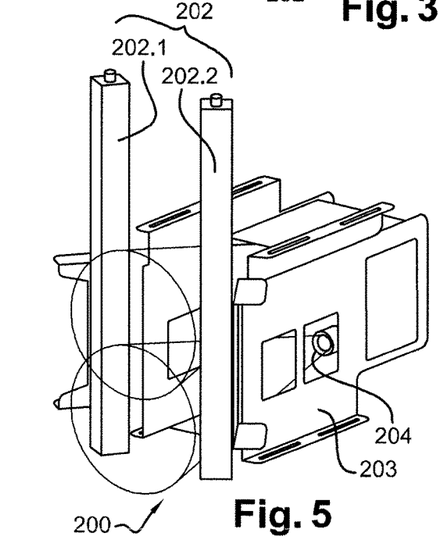
FIG. 5 is a schematic perspective view of the checking device of FIG. 4.
Figures 7, 8, 9, 10:
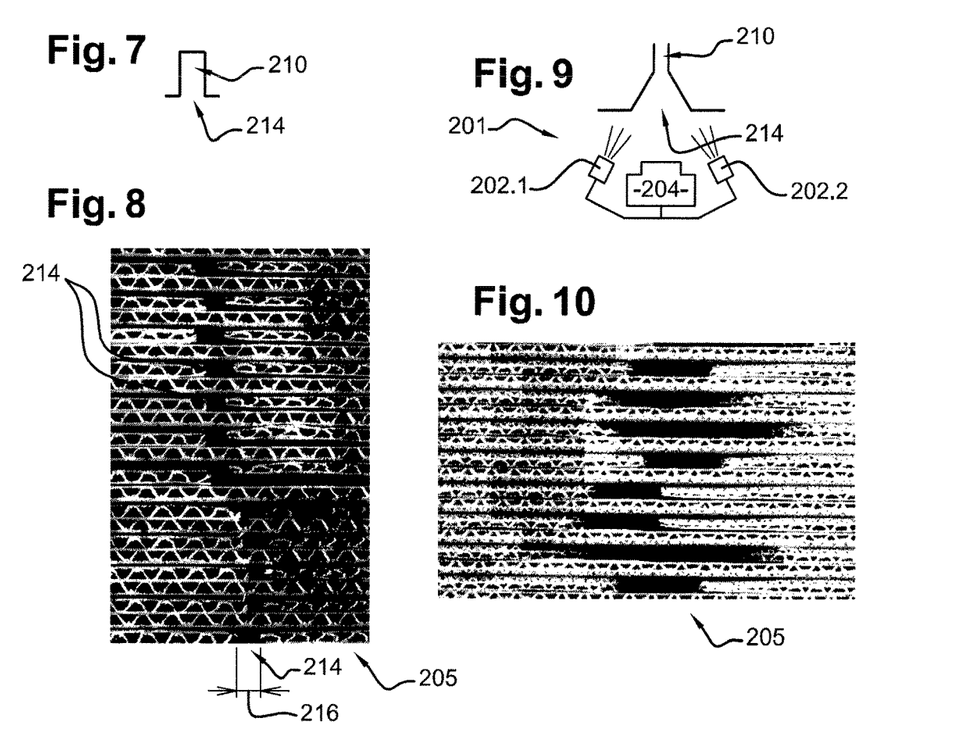
FIG. 7 is a diagram illustrating a first type of slot to be checked.
FIG. 8 is a plural image of a pack of foldable boxes having slots of the first type, the plural image having been formed by an imaging device belonging to the checking device of FIG. 3.
FIG. 9 is a schematic view of the checking device of FIG. 3, during a step of a checking method according to the invention, in which two illumination sources simultaneously illuminate a pack of foldable boxes having a second type of slot to be checked.
FIG. 10 is a plural image resulting from the step shown in FIG. 9.

The image processing system 206 is configured for:

i) detecting each peripheral end 214 (FIGS. 4 and 8) in the plural image, that is to say all the peripheral ends 214 of the slots 210 defined by the foldable boxes composing the pack 201, ii) generating a set of data representing the geometry of each peripheral end 214, iii) analyzing the set of data so as to determine the width of each lateral interval 216 (FIGS. 4 and 8).

In the example of FIGS. 2 to 6, the image processing system 206 is also configured for:

a) detecting the boundaries of the peripheral face 212 perpendicularly to the largest dimension of the peripheral pack face 212, b) measuring a reference level of brightness between one of these boundaries of the peripheral pack face 212 and an edge 205 of the plural image, and c) generating a binary plural image 207 (FIGS. 17 to 19) by using this reference brightness level to perform a thresholding operation on the plural image 205.

Figure 17:
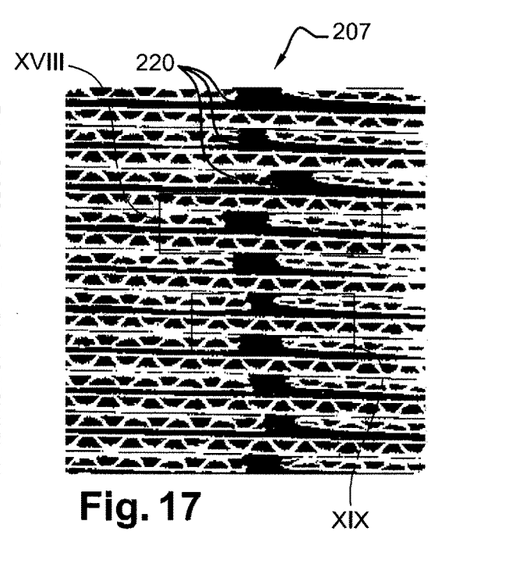
FIG. 17 is a binary image obtained from the image of FIG. 16.
Figures 18, 19:
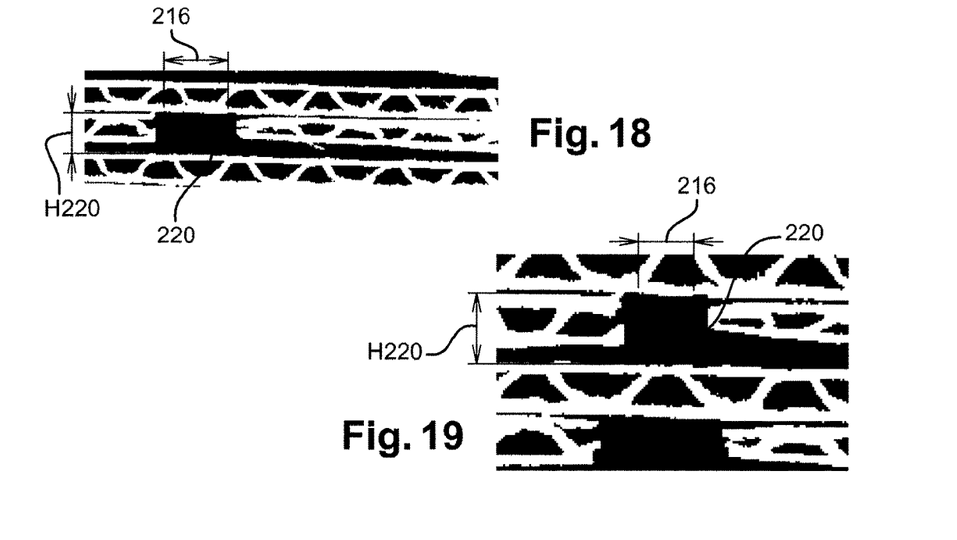
FIG. 18 is a view on a larger scale of the detail XVIII in FIG. 17, showing a step of the checking method shown in FIG. 15.
FIG. 19 is a view on a larger scale of the detail XIX in FIG. 17, showing a step of the checking method shown in FIG. 15.

On the basis of a binary plural image 207, the image processing system 206 can then:

iv) extract dark objects 220 from each binary plural image 207, v) compare the height H220 of each dark object 220 with the nominal thickness of a foldable box 1 in the folded state, vi) select each dark object 220 having a height H220 equivalent to the nominal thickness of a foldable box in the folded state subject to a predetermined tolerance, so that each dark object of the height is one folded box, and its folded condition can be singled out for consideration by the image processing system, vii) detect, in each binary plural image 207, the boundaries of the foldable boxes forming the ends of the pack 201 perpendicularly to the largest dimension of a foldable box 1 in the folded state, and viii) discriminate each foldable box in the pack 201; the image processing system 206 carries out the discrimination of each foldable box by processing a binary plural image 207 (FIGS. 17 to 19).

The image processing system 206 then generates a set of data representing the geometry of the peripheral ends 214 of the slots 210, so as to determine the width of each lateral interval 216, for all the foldable boxes appearing in the binary plural image 207, and therefore in the plural image 205.

By processing a single plural image 205, the image processing system 206 can thus determine the lateral intervals 216 of the slots 210 of all the foldable boxes composing a pack 201.

In practice, the image obtained from one camera 204 is larger than the plural image 205. The plural image 205 is the useful portion of the image obtained from a camera 204, that is the portion where the lateral ends can be detected. In other words, the other portions of the image obtained from a camera 204 show no lateral ends. The useful portion can be selected automatically on the basis of the dimensions of each foldable box 1, with a margin intended to compensate for imperfect alignment of the foldable boxes in the pack 201. By reducing the image obtained from a camera 204 to the useful portion forming a plural image 205, the duration of the image processing can be minimized.

FIGS. 7 and 9 show schematically, in cross section, the geometry of two types of slots. FIG. 7 shows a first type of slot called "straight", because the edges of the slot are parallel to one another. FIG. 9 shows a second type of slot called "V-shaped", because the edges diverge obliquely toward the peripheral end.

FIGS. 8 and 10 show the plural images 205 obtained for the first type of slot (FIG. 7) and for the second type of slot (FIG. 9), respectively, when the illumination sources 202.1 and 202.2 simultaneously illuminate the peripheral pack face 212.

The plural image 205 of FIG. 8 has peripheral ends whose edges have a high level of contrast. That is because the edges defining the slot do not project into the slot. The image processing system 206 can therefore easily process the plural image 205 of FIG. 8, in order to detect the peripheral ends of the slots and determine the width of each lateral interval.

Conversely, the plural image 205 of FIG. 10 has peripheral ends whose edges have a low level of contrast, because the slot is of the "V-shaped" type and the end edges of the flaps extend into the slot. The image processing system 206 therefore finds it more difficult to process the plural image 205 of FIG. 10 than the plural image of FIG. 8.

Figure 11:
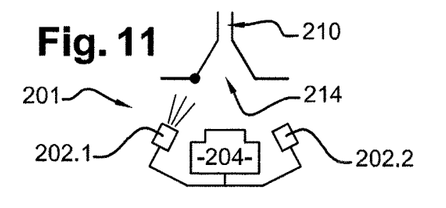
FIGS. 11 and 12 are schematic views of the checking device of FIG. 3, during a step of a checking method according to the invention, in which two illumination sources successively illuminate a pack of foldable boxes.
Figure 12:
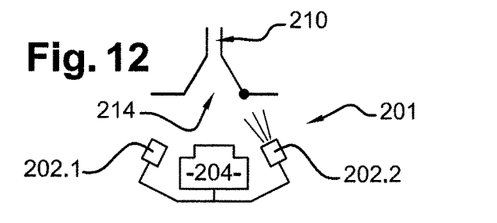
Figure 13:
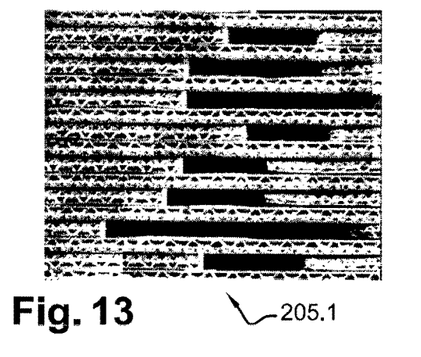
FIGS. 13 and 14 are images resulting from the steps shown in FIGS. 11 and 12 respectively.

The two illumination sources 202.1 and 202.2 are arranged on either side of the cameras 204. As shown in FIGS. 11 and 13, the illumination sources 202.1 and 202.2 are configured to illuminate the same peripheral pack face 212 successively. Thus each camera 204 successively forms two different plural images 205.1 and 205.2, visible in FIGS. 12 and 14, for the same peripheral pack face 212.

Figure 14:
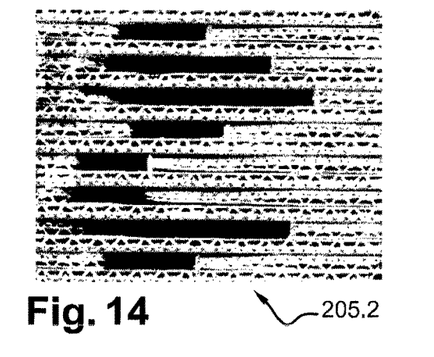

The plural image 205.1 is formed during the illumination by the illumination source 202.1, and the plural image 205.2 is formed during the illumination by the illumination source 202.2. In the plural image 205.1, the left-hand boundary of each peripheral end 214 has a high contrast level, and in the plural image 205.2 the right-hand boundary of each peripheral end 214 has a very high contrast level. The illumination system 202 is configured to illuminate the peripheral pack face 212 in a pulsed manner. The duration of an illumination pulse is about 20 ms in this case. Between the two pulses, the pack 201 remains immobile, to ensure that the two successively formed images coincide.

The image processing system 206 then processes the plural images 205.1 and 205.2 for the purpose of:
detecting the left and right boundaries of each peripheral end 214,
generating a set of data representing the geometry of each peripheral end 214,
analyzing said set of data so as to determine the width of each lateral interval 216.

This configuration of the illumination sources 202.1 and 202.2 enables the illumination system 202 to produce alternating illumination, which improves the detection of all the peripheral ends 214 of the V-shaped slots.

Figure 15:
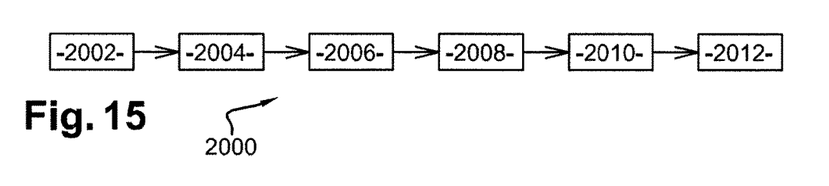
FIG. 15 is a flow chart illustrating a checking method according to the invention.
Figure 16:
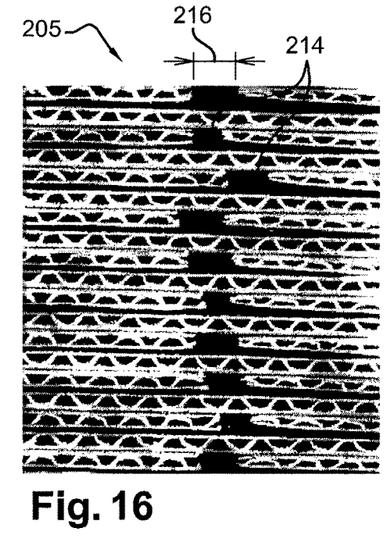
FIG. 16 is an image of a pack of foldable boxes having slots of the first type, the image resulting from a step of the checking method shown in FIG. 15.

In use, the checking device 200 is operated according to a checking method 2000 according to the invention, illustrated in FIG. 15. The checking method 2000 comprises the steps of:
2002. illuminating, by means of the illumination system 202, a peripheral pack face 212,
2004. forming, by means of each camera 204, plural images 205 of the peripheral pack face 212 when the illumination system 202 illuminates the peripheral pack face 212,
2006. actuating the image processing system 206 for the purpose of:
2008. i) detecting each peripheral end 214 in each plural image 205 of the peripheral pack face 212,
2010. ii) generating a set of data representing the geometry of each peripheral end 214, and
2012. iii) analyzing the set of data so as to determine the width of each lateral interval 216.

Figure 20:
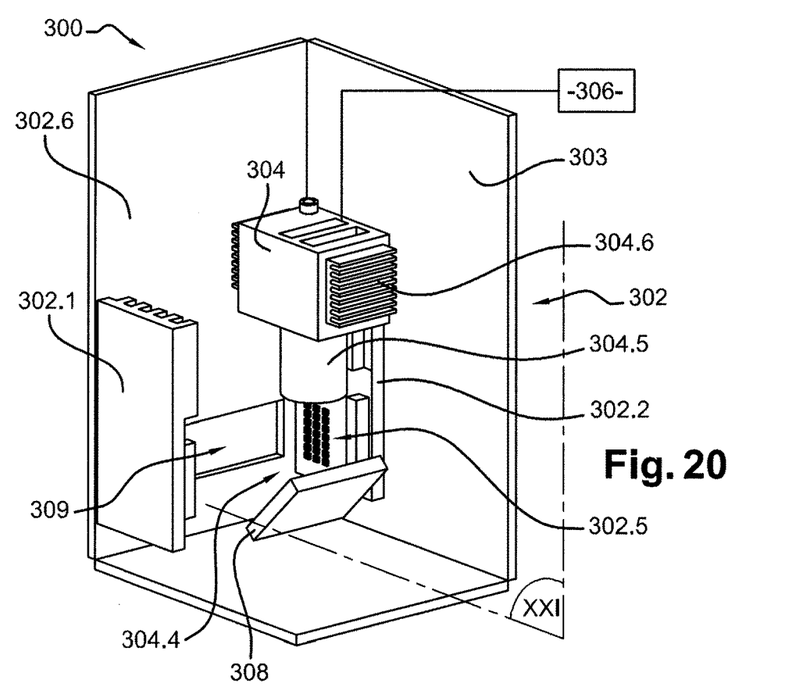
FIG. 20 is a schematic perspective view showing part of a checking device according to a second embodiment of the invention and comprising a line scan camera.
Figure 21:
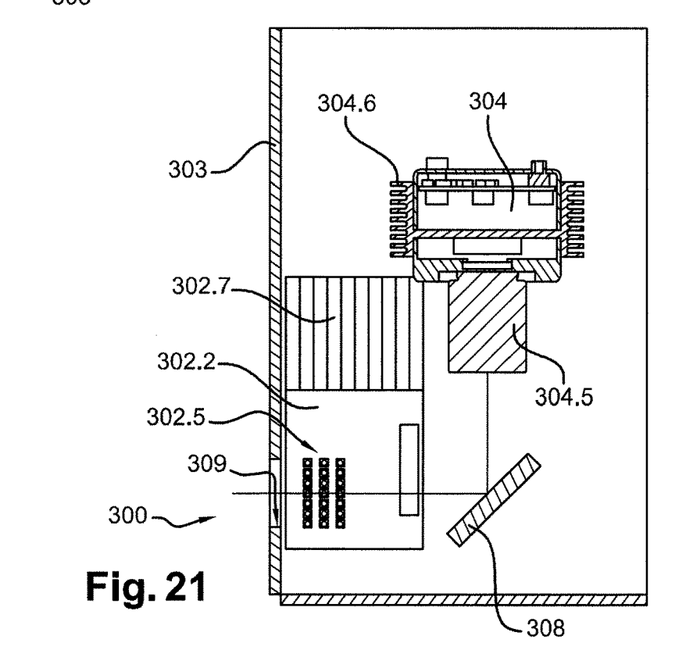
FIG. 21 is a cross section along the plane XXI in FIG. 20.

FIGS. 20 and 21 show part of a checking device 300 according to a second embodiment of the invention. To the extent that the checking device 300 is similar to the checking device 200, the description of the checking device 200 given above in relation to FIGS. 1 to 19 can be transposed to the checking device 300, with the exception of the notable differences stated below.

Any element of the checking device 300 which is identical or similar, in its structure and/or function, to an element of the checking device 200 carries the same reference, increased by 100. Thus an illumination system 302 with two light sources 302.1 and 302.2, a framework 303, a camera 304 and an image processing system 306 are defined.

The checking device 300 differs from the checking device 200, notably, in that the camera 304 is a line scan camera, whereas the checking device 200 comprises two matrix cameras 204. A line scan camera is a camera in which the photosensitive part is composed of a line of sensors (with a dimension of 1×n). The sensors may be CCD ("Charge-Coupled Device") sensors, or CMOS ("Complementary Metal-Oxide-Semiconductor") sensors. The camera 304 is configured to receive an optical beam 304.4.

The checking device 300 also differs from the checking device 200, notably, in that its imaging device is formed by a single camera 304, whereas the imaging device of the checking device 200 comprises two cameras 204. The camera 304 has an optical correction device 304.5 and a heat sink 304.6 configured to cool the camera 304 in use.

Furthermore, the checking device 300 differs from the checking device 200, notably, in that each illumination source 302.1 and 302.2 is composed of light-emitting diodes (LED) 302.5 arranged in a rectangular matrix, whereas the illumination system 202 is formed by two linear illumination sources. Each illumination source 302.1 and 302.2 comprises a respective heat sink 302.6 and 302.7.

Additionally, the checking device 300 differs from the checking device 200, notably, in that the checking device 300 further comprises a reflecting mirror 308 arranged so as to reflect the light received from each pack of foldable boxes toward the camera 304. This reflecting mirror 308 makes it possible to form a compact checking device 300. Each illumination source 302.1 and 302.2 directly illuminates each pack of foldable boxes through an aperture 309 formed in the framework 303.

In use, the checking device 300 can be operated according to the checking method 2000 illustrated in FIG. 15.

Clearly, the present invention is not limited to the specific embodiments described in the present patent application, nor to embodiments within the compass of a person skilled in the art. Other embodiments may be envisaged without departing from the scope of the invention, using any element equivalent to an element indicated in the present patent application.

The invention claimed is:

1. A checking device for checking the quality of foldable boxes and when each foldable box is in a folded state, in which each foldable box comprises at least two flaps folded toward each other and each folded over a flap having a free end, the free ends define and are separated by a slot, the slot has a peripheral end opening on a peripheral face of the foldable box and the slot delimits a lateral interval between the free ends of the two flaps at the peripheral face;
the checking device comprising:
an illumination system configured for illuminating the foldable boxes in the folded state at the peripheral face, the illumination system being configured to illuminate a pack formed of superimposed or juxtaposed ones of the foldable boxes, wherein the pack has at least one peripheral pack face defined by respective peripheral faces of all the foldable boxes comprising the pack;
at least one imaging device configured for forming images of the foldable boxes in the folded state, the at least one imaging device being configured to form at least one plural image representing at least a part of the peripheral pack face when the illumination system illuminates the peripheral pack face; and
at least one image processing system configured for:
i) detecting each peripheral end of a slot in the at least one plural image;
ii) generating a set of data representing a geometry of each peripheral end; and
iii) analyzing the set of data to determine the width of each lateral interval,
wherein the illumination system comprises two illumination sources arranged respectively on two different sides of the at least one imaging device, the two different sides of the at least one imaging device respectively being on two different sides of a longitudinal vertical plane extending in a direction of circulation of and extending along a centerline of a width of a conveying device conveying the foldable boxes, the two different sides of the at least one imaging device being parallel to the longitudinal vertical plane, the illumination sources being configured for successive illumination of the same peripheral face of each foldable box in the folded state, so that the at least one imaging device successively forms two different images of the same peripheral face of each foldable box in the folded state.

2. The checking device according to claim 1, wherein:
the image processing system is further configured for:
iv) extracting dark objects from each of the at least one plural image;
v) comparing a height of each dark object with a thickness of a foldable box in the folded state, wherein the height is measured perpendicularly to the largest dimension of the foldable box in the folded state, and
vi) selecting each dark object having a height that is equivalent to the thickness of a foldable box in the folded state subject to a predetermined tolerance, wherein each selected dark object corresponds to a lateral interval.

3. The checking device according to claim 2, wherein each plural image is a binary image; and
the image processing system is further configured for:
vii) detecting, in each binary plural image, boundaries of the foldable boxes forming the ends of the pack perpendicularly to the largest dimension of a foldable box in the pack then in the folded state; and
viii) discriminating each foldable box in the pack.

4. The checking device according to claim 1, wherein:
the image processing system is also configured for:
iv) comparing the width of each lateral interval with a predetermined lower limit and a predetermined upper limit; and
v) generating an anomaly signal if the width of a lateral interval is either below the predetermined lower limit or above the predetermined upper limit.

5. The checking device according to claim 1, wherein the at least one imaging device is a matrix camera.

6. The checking device according to claim 1, wherein the at least one imaging device comprises a line scan camera configured to form an image of a respective one of the peripheral faces of each foldable box; and
the conveying device is configured and operable for moving each foldable box relative to the line scan camera.

7. The checking device according to claim 6, wherein the at least one imaging device comprises two imaging devices placed at two different heights of the pack to form plural images of a lower part and an upper part, respectively, of the peripheral pack face.

8. The checking device according to claim 1, wherein the illumination system comprises at least one illumination source selected from the group consisting of fluorescent tubes, discharge lamps, light-emitting diodes, and a column of light-emitting diodes.

9. The checking device according to claim 8, wherein the illumination system is configured to illuminate in a pulsed manner a peripheral face of each foldable box in the folded state.

10. A manufacturing installation, for manufacturing foldable boxes, when each foldable box is in a folded state, each foldable box comprising panels linked by folds and comprising at least two folded flaps folded toward each other and each folded over a flap having a free end, the free ends defining and being separated by a slot;
the manufacturing installation comprising:
a gluing device configured to apply glue to a gluing area of each foldable box;
a folding device configured to fold the panels so as to glue an area to be glued onto the gluing area;
a stacking device configured for stacking the foldable boxes in the folded state;
a conveying device, configured to in succession place each foldable box at the gluing device, then at the folding device to be folded, then in the stacking device for the folded boxes to be stacked; and
the checking device according to claim 1, the checking device being placed downstream of the stacking device.

11. The manufacturing installation according to claim 10, further comprising another checking device, in addition to the checking device, so as to form respective images of two peripheral pack faces.

12. A checking method for checking the quality of foldable boxes, wherein, when each foldable box is in a folded state, each foldable box comprises at least two flaps which are separated by a slot, the slot having a peripheral end opening on a peripheral face of the foldable box and delimiting a lateral interval between the two flaps;
the checking method comprising the steps of:
illuminating, with an illumination system, a pack of the foldable boxes in the folded state, wherein the pack is formed of superimposed or juxtaposed foldable boxes, and the pack has at least one peripheral pack face defined by peripheral faces of all the foldable boxes composing the pack;
forming, with at least one imaging device, images of the foldable boxes in the folded state,
wherein each of the images comprises at least one plural image representing at least a part of the peripheral pack face when the illumination system illuminates the peripheral pack face; and
actuating at least one image processing system for the purpose of:
i) detecting at least one peripheral end in the at least one plural image;
ii) generating a set of data representing the geometry of each peripheral end; and
iii) analyzing the set of data for determining the width of each lateral interval,
wherein the illumination system comprises two illumination sources arranged respectively on two different sides of the at least one imaging device, the two different sides of the at least one imaging device respectively being on two different sides of a longitudinal vertical plane extending in a direction of circulation of and extending along a centerline of a width of a conveying device conveying the foldable boxes, the two different sides of the at least one imaging device being parallel to the longitudinal vertical plane, the illumination sources being configured for successive illumination of the same peripheral face of each foldable box in the folded state, so that the at least one imaging device successively forms two different images of the same peripheral face of each foldable box in the folded state.

* * * * *